(12) United States Patent
An et al.

(10) Patent No.: US 9,581,551 B2
(45) Date of Patent: Feb. 28, 2017

(54) COLOR-CHANGE SENSOR USING FILM FOR DETECTING HARMFUL MATERIAL

(71) Applicant: RESEARCH & BUSINESS FOUNDATION SUNGKYUNKWAN UNIVERSITY, Suwon-si (KR)

(72) Inventors: Jeong Ho An, Seoul (KR); Dong Jun Chung, Yongin-si (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 0 days.

(21) Appl. No.: 14/814,663

(22) Filed: Jul. 31, 2015

(65) Prior Publication Data

US 2016/0033419 A1 Feb. 4, 2016

(30) Foreign Application Priority Data

Jul. 31, 2014 (KR) .................. 10-2014-0097991
Nov. 27, 2014 (KR) .................. 10-2014-0167275

(51) Int. Cl.
*G01N 31/22* (2006.01)
*G01N 33/52* (2006.01)
(Continued)

(52) U.S. Cl.
CPC .............. *G01N 21/78* (2013.01); *G01N 21/29* (2013.01); *G01N 21/77* (2013.01); *G01N 31/22* (2013.01); *G01N 33/52* (2013.01); *G01N 33/521* (2013.01); *A61L 2/28* (2013.01); *B01L 3/5023* (2013.01); *B01L 2300/0816* (2013.01); *G01N 21/783* (2013.01); *G01N 31/223* (2013.01);
(Continued)

(58) Field of Classification Search
CPC ...... G01N 31/22; G01N 21/78; G01N 31/223; G01N 21/783; G01N 31/224; G01N 33/52; G01N 33/521; G01N 33/525; G01N 33/526; G01N 21/77; G01N 33/523; G01N 21/29; G01N 33/0044; G01N 33/54386

See application file for complete search history.

(56) References Cited

U.S. PATENT DOCUMENTS

| 4,619,793 | A | | 10/1986 | Lee |
| 5,286,624 | A | * | 2/1994 | Terashima ............. G01N 31/22 422/423 |

(Continued)

FOREIGN PATENT DOCUMENTS

| JP | 8-502549 A | 3/1996 |
| KR | 10-0305660 B1 | 9/2001 |

OTHER PUBLICATIONS

O.S. Wolfbeis, "Chemical Sensing Using Indicator Dyes", Optical Fiber Sensors, vol. IV, Chapter 8, 1997, pp. 53-107.

*Primary Examiner* — Jennifer Wecker
(74) *Attorney, Agent, or Firm* — NSIP Law

(57) ABSTRACT

The following description relates to a composite for a harmful material-detecting sensor, which includes a dye having a color-change function by reaction with acid or base and a polymer material, a method for producing the composite for the harmful material-detecting sensor, and a low-cost film-type color change harmful material sensor, which includes the composite for the harmful material-detecting sensor so as to quickly detect a harmful material and can be carried by an individual.

11 Claims, 11 Drawing Sheets
(4 of 11 Drawing Sheet(s) Filed in Color)

(51) Int. Cl.
*G01N 31/00* (2006.01)
*G01N 21/78* (2006.01)
*G01N 21/77* (2006.01)
*G01N 21/29* (2006.01)
*B01J 19/00* (2006.01)
*A61L 2/28* (2006.01)
*G01N 21/75* (2006.01)
*G01N 33/543* (2006.01)
*B01L 3/00* (2006.01)
*G01N 33/00* (2006.01)

(52) U.S. Cl.
CPC ....... *G01N 31/224* (2013.01); *G01N 33/0044* (2013.01); *G01N 33/523* (2013.01); *G01N 33/525* (2013.01); *G01N 33/526* (2013.01); *G01N 33/54386* (2013.01); *G01N 2021/757* (2013.01)

(56) References Cited

U.S. PATENT DOCUMENTS

| | | | | |
|---|---|---|---|---|
| 2002/0068364 A1* | 6/2002 | Arai | ...................... | G01N 31/223 436/113 |
| 2008/0107566 A1* | 5/2008 | Abe | ...................... | B01L 3/5023 422/68.1 |
| 2009/0007815 A1* | 1/2009 | Hampden-Smith | | C09K 11/7769 106/31.13 |
| 2009/0023217 A1* | 1/2009 | Lacy | .................... | G01N 31/228 436/2 |
| 2012/0156513 A1* | 6/2012 | Kawabe | .................. | B32B 27/08 428/483 |
| 2015/0004707 A1* | 1/2015 | Nair | .......................... | A61L 2/28 436/1 |

* cited by examiner

FIG. 6A

| Gas | Dye | pH range for color change | |
|---|---|---|---|
| HF, Hydrogen fluoride | Bromophenol Blue | 3.0-4.6 | |
| | Bromocresol Green | 3.8-5.4 | |
| HCl, Hydrogen chloride | Bromophenol Blue | 3.0-4.6 | |
| | Bromocresol Green | 3.8-5.4 | |
| $Cl_2$, Chlorine | Chlorophenol Red | 4.8-6.4 | |
| $NH_3$, Ammonia | Bromophenol Blue | 3.0-4.6 | |
| | Bromocresol Green | 3.8-5.4 | |
| HCHO, Formaldehyde | Chlorophenol Red | 4.8-6.4 | |
| | Bromocresol Purple | 5.2-6.8 | |

FIG. 6B

| Dye | | pH range for color change |
|---|---|---|
| Bromophenol Blue | 3.0-4.6 | |
| Bromocresol Green | 3.8-5.4 | |
| Chlorophenol Red | 4.8-6.4 | |
| Bromocresol Purple | 5.2-6.8 | |

*FIG. 7*

| GAS | DYE | BEFORE EXPOSURE | AFTER EXPOSURE |
|---|---|---|---|
| AMMONIA | BROMOPHENOL BLUE (BPB) | | |
| | BROMOCRESOL GREEN (BCG) | | |
| HYDROFLUORIC ACID | BROMOPHENOL BLUE (BPB) | | |
| | BROMOCRESOL GREEN (BCG) | | |
| HYDROCHLORIC ACID | BROMOPHENOL BLUE (BPB) | | |
| | BROMOCRESOL GREEN (BCG) | | |
| FORM ALDEHYDE | BROMOCRESOL PURPLE (BCP) | | |
| | CHLOROPHENOL RED (CPR) | | |

*FIG. 8*

|  | SAMPLE 1 | SAMPLE 2 | SAMPLE 3 |
|---|---|---|---|
| BEFORE DISSOLUTION TEST | | | |
| AFTER DISSOLUTION TEST | | | |

COLOR-CHANGE SENSOR USING FILM FOR DETECTING HARMFUL MATERIAL

CROSS-REFERENCE TO RELATED APPLICATION

This application claims the benefit under 35 USC 119(a) of Korean Patent Application No. 10-2014-0097991 filed on Jul. 31, 2014 and Korean Patent Application No. 10-2014-0167275 filed on Nov. 27, 2014, in the Korean Intellectual Property Office, the entire disclosures of which is incorporated herein by reference for all purposes.

TECHNICAL FIELD

The present disclosure described herein pertain generally to a composite for a harmful material-detecting sensor, which includes a dye having a color change function by reaction with acid or base and a polymer material, a method for producing the composite for the harmful material-detecting sensor, and a low-cost film-type color change harmful material sensor, which includes the composite for the harmful material-detecting sensor so as to quickly detect a harmful material and can be carried by an individual.

BACKGROUND

As leakage of harmful materials in various industrial sites and during transportation causes important social issues further to loss of life, there has been necessity for a technology, which is capable of early detecting harmful materials. As equipment for detecting a harmful material, an expensive stationary sensor system has already been mounted and operated in most processes, and a portable device achieved through miniaturization of an analysis device has also been commercialized. However, these devices lack economic rationality so that they would not be supplied to and used by an individual operator. In order to avoid loss of life upon an accident of leakage of a harmful material, initial responsive measures are the most critical, and for rapid initial responsive measures, development of a detection system that can be supplied to individuals, especially, a sensor technology that enables recognition by an individual operator without requiring special measurement equipment is demanded. As this type of a detection kit, the color change badge system (Chameleon badge system) of Morphix Technology has been globally commercialized, and this product puts a reagent in a solution form causing a color change reaction in a pouch made of a material, through which a harmful gas can pass. The product exhibits difference in reaction time depending on materials to be detected, and for example, requires exposure time of at least 1 minute to 15 minutes in case of ammonia; and since the product is in the pouch form, there is limitation in miniaturization for reduction of a volume, and thus, the product is inappropriate in a size to carry and operate. In addition, with respect to other portable products, there is a product, which was developed by Drager in Germany and RAE systems in U.S.A. and manufactured to be in a tube form with a color change detection material, and this product is a type of a reagent and has a limit in that a harmful material should be concentrated and introduced into the tube.

Meanwhile, there have been attempts, although have not reached the commercial development stage yet, to detect multiple harmful materials at a time by printing a chemoresponsive dye or a fluorophore on a reverse phase silica gel plate, an acid free paper, a porous cellulose acetate, or a film of porous polyvinylidene difluoride through inkjet technology; however, since this method should conduct the detection by using digital imaging, rather than detection through eye observation, the product is not substantially considered an individual portable product.

Meanwhile, Korean Patent No. 10-0305660 describes a sulfur compound-based gas sensor, to which CuO is added by using a double ion beam method.

SUMMARY

In view of the foregoing, embodiments provide a composite for a harmful material-detecting sensor, which includes a dye dispersed within a water-soluble polymer matrix, a method for producing the composite for the harmful material-detecting sensor, and a harmful material-detecting sensor, which includes the composite for the harmful material-detecting sensor.

However, the problems sought to be solved by the present disclosure are not limited to the above description, and other problems can be clearly understood by those skilled in the art from the following description.

An aspect of the present disclosure, there is provided a composite for a harmful material-detecting sensor, including a dye dispersed in a water-soluble polymer matrix.

Another aspect of the present disclosure, there is provided a method for producing a composite for a harmful material-detecting sensor, including: adding a dye to a water-soluble polymer solution to obtain an aqueous solution of the water-soluble polymer and the dye; applying the aqueous solution of the water-soluble polymer and the dye onto a substrate to form a composite film; and annealing the composite film as a post-treatment.

Still another aspect of the present disclosure, there is provided a harmful material-detecting sensor, comprising the composite for the harmful material-detecting sensor according to the first aspect.

In accordance with the embodiments, it is possible to produce a film-type color change sensor by anchoring a color change dye with polymers, which are water-soluble and provide water resistance through a crystallization process after film formation or have a certain level or higher water content. Further, it is possible to produce a film-type sensor, which provides more improved water resistance by double-coating the polymers, and simultaneously, minimizes time for harmful material detection.

In accordance with the embodiments, it is possible to provide a film-type sensor, which includes a polymer material and a dye, enables a user to rapidly recognize the presence of a harmful material at low costs without special equipment, is easy to carry, and can be used in various environments, e.g., in various temperature and humidity environments.

BRIEF DESCRIPTION OF THE DRAWINGS

The patent or application file contains a least one drawing executed in color. Copies of this patent or patent application publication with color drawing(s) will be provided by the Office upon request and payment of the necessary fee.

FIG. 6A shows standard color change depending on harmful materials, in an embodiment of the present disclosure.

FIG. 6B shows color change of used dyes, in an Example of the present disclosure.

FIG. 7 shows color change before and after each dye used in producing a film is exposed to a harmful material, in an Example of the present disclosure.

FIG. 8 illustrates that water resistance can be improved depending on a heat treatment condition after film production, in an Example of the present disclosure.

DETAILED DESCRIPTION

Figure 1:
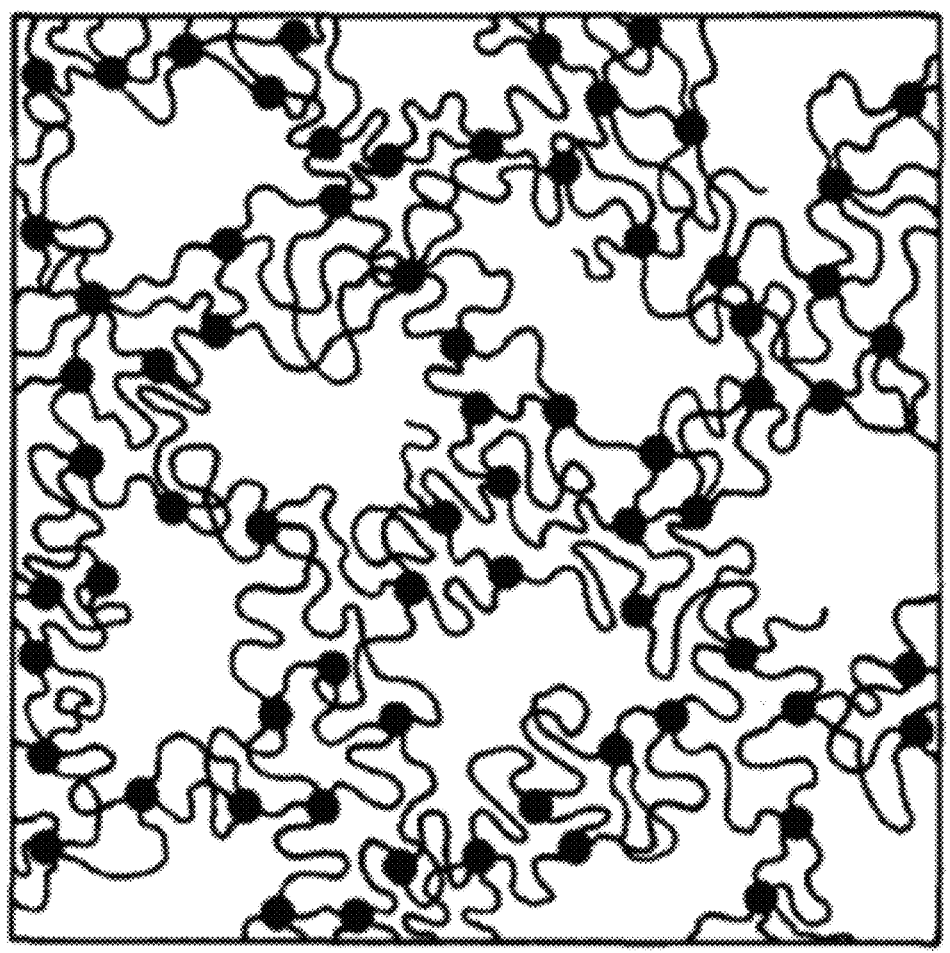
FIG. 1 is a schematic view of a crystal structure, in an embodiment of the present disclosure.

Hereinafter, embodiments will be described in detail with reference to the accompanying drawings so that inventive concept may be readily implemented by those skilled in the art. However, it is to be noted that the present disclosure is not limited to the embodiments but can be realized in various other ways. In the drawings, certain parts not directly relevant to the description are omitted to enhance the clarity of the drawings, and like reference numerals denote like parts throughout the whole document.

Throughout the whole document, the terms "connected to" or "coupled to" are used to designate a connection or coupling of one element to another element and include both a case where an element is "directly connected or coupled to" another element and a case where an element is "electronically connected or coupled to" another element via still another element.

Throughout the whole document, the term "on" that is used to designate a position of one element with respect to another element includes both a case that the one element is adjacent to the another element and a case that any other element exists between these two elements.

Throughout the whole document, the term "comprises or includes" and/or "comprising or including" used in the document means that one or more other components, steps, operations, and/or the existence or addition of elements are not excluded in addition to the described components, steps, operations and/or elements.

Throughout the whole document, the terms "about or approximately" or "substantially" are intended to have meanings close to numerical values or ranges specified with an allowable error and intended to prevent accurate or absolute numerical values disclosed for understanding of the present invention from being illegally or unfairly used by any unconscionable third party.

Throughout the whole document, the term "step of" does not mean "step for."

Throughout the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Throughout the whole document, the description "A and/or B" means "A or B, or A and B."

Embodiments of the present disclosure have been described in detail, but the present disclosure may not be limited to the embodiments.

An aspect of the present disclosure provides a composite for a harmful material-detecting sensor, which includes a dye dispersed in a water-soluble polymer matrix.

In an embodiment of the present disclosure, the dye may react with the harmful material to exhibit its color change, but not be limited thereto. The dye may be a material, which can be dissolved in water or a polar solvent. As the dye, any conventionally known dyes may be used without limitation, and the dye may include, for example, a dye selected from the group consisting of bromophenol blue, bromocresol green, chlorophenol red, bromocresol purple, alizarin red S, alizarin yellow GG, alizarin yellow R, brilliant yellow, bromothymol blue, Congo red, dimethyl yellow, metacresol purple, methyl red, methyl green, methyl orange, phenolphthalein, Clayton yellow, cresol red, crystal violet, erythrosin, malachite green, metanil yellow, neutral red, phenol red, para-methyl red, para-nitrolphenol, quinaldine red, thymolphtalein, thymol blue, resazurin, and combinations thereof, but not be limited thereto.

In an embodiment of the present disclosure, the harmful material may include a member selected from the group consisting of ammonia ($NH_3$), hydrochloric acid (HCl), hydrofluoric acid (HF), formaldehyde (HCHO), chlorine ($Cl_2$), hydrogen sulfide, dimethyl amine, diethyl amine, triethyl amine, methyl amine, sulfur dioxide, nitric acid, and combinations thereof, but not be limited thereto. In addition, the harmful material may be acidic or alkaline.

In an embodiment of the present disclosure, the composite for the harmful material-detecting sensor may be in a form of film, but not be limited thereto.

In an embodiment of the present disclosure, the film may include a single film layer or multiple film layers, but not be limited thereto. If the film forms multiple film layers, the water resistance of the composite for the harmful material-detecting sensor may be improved.

In an embodiment of the present disclosure, the film may include a crystallized film, but not be limited thereto. In addition, the film may be crystallized to improve the water resistance thereof, but the present disclosure may not be limited thereto.

In order to solve the problem of the conventional portable harmful material-detecting kit, a smaller and more affordable device, which enables rapid recognition of an operator without requiring special equipment and can be used in various environment conditions, is demanded. As means to solve the above-described problem, there may be a method of producing a film by mixing a color change dye with a polymer material. FIG. 6A shows standard color change of the dye depending on harmful materials.

In an embodiment of the present disclosure, the water-soluble polymer matrix may include poly(vinyl alcohol) (PVA) or poly(vinyl butyral) (PVB), but not be limited thereto. For example, the water content may range from about 1% to about 20% or from about 4% to about 15%, but not be limited thereto.

In an embodiment of the present disclosure, the water-soluble polymer matrix may contain water in a certain content or more, but not be limited thereto.

In order to structure the harmful material-detecting film-type sensor, the following technical requirements should be met. There are considerable types of dyes, which exhibit color change according to presence of acid or base, including synthetic materials and natural materials. Since a common color change dye exhibits color change depending on a quantity of $H^+$ or $OH^-$ ions present in an aqueous solution, it needs a certain amount of water. Accordingly, the polymer material used to introduce the color change dye into the film needs to have a significant level of water solubility.

A final film, which retains the water solubility and includes the color change dye as described above, is required to be used in various environments, i.e., various temperature or humidity conditions. Most water-soluble polymers are possibly dissolved when they contact with water even after a solid film is formed, and even though the polymers are not fully dissolved, since the color change dye contained in the polymer film is also water-soluble, the dye is possibly leaked outward. Accordingly, a method capable of minimizing the dissolution of the polymer film or the leakage of the color change dye needs to be provided.

With respect to the polymer material used for detection of a harmful material, a dye should be easily dissolved or dispersed in the polymer material, and since the polymer material and the dye should not react with each other or should not form a strong complex, an ionic polymer reacting with a dye cannot be used. In addition, total detection time needs to be short, and the total detection time includes movement time of a material to be detected and reaction time of a color change material. The material to be detected is acidic or alkaline and is not delivered to the color change material if it contains no water, and since the dye also exhibits color change according to the $H^+$ or $OH^-$ ions, the detection is impossible if no water exists. Reaction Formula 1 below shows an example for a process of structure change of the color change dye.

In addition, the polymer material is required to form a film, which can suppress permeation of contaminants and an excessive amount of water while allowing penetration of a harmful gas and a small amount of water.

In an embodiment of the present disclosure, the method for producing the harmful material-detecting film-type sensor may use a polymer material, which retains sufficient water solubility so as to maintain the detection function after the process of the mixture with the dye and the film formation and provides a certain level of water resistance.

Figure 2:
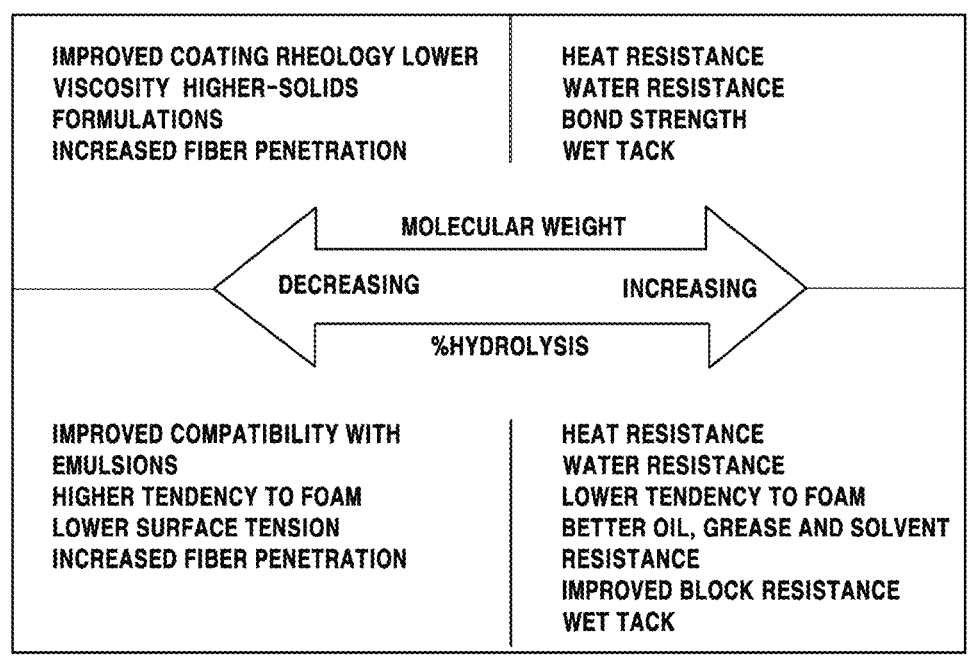
FIG. 2 shows performance change according to increase and decrease of a molecular weight and hydrolysis, in an embodiment of the present disclosure.
Figure 3:
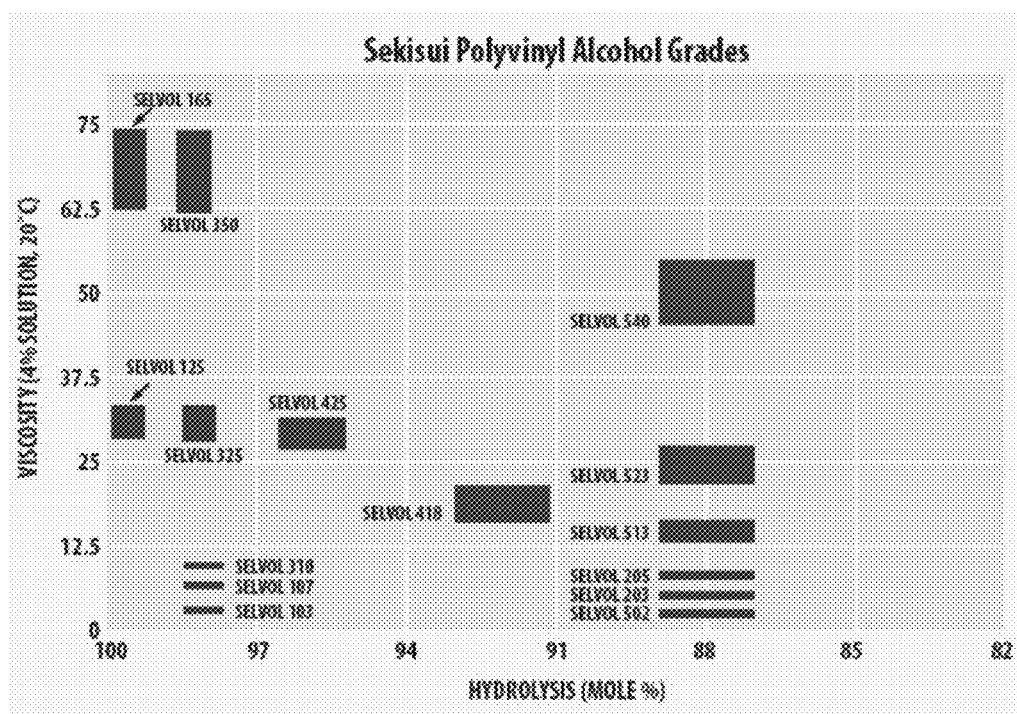
FIG. 3 shows a grade of polyvinyl alcohol) according to viscosity and hydrolysis, in an embodiment.

In an embodiment of the present disclosure, with regard to an example for the polymer having the above-described characteristics, poly(vinyl alcohol) is not industrially polymerized directly from monomers and may be produced by first polymerizing poyl(vinyl acetate), and then, alcoholyzing the same (Reaction Formula 2). Accordingly, the material commonly called poly(vinyl alcohol) is a copolymer of vinyl alcohol and vinyl acetate. The alcoholysis reaction cannot proceed fully (100%), and accordingly, there are significantly various grades of poly(vinyl alcohol) depending on a molecular weight of poly(vinyl acetate), which is the source material, and the extent of the alcoholysis (FIG. 2 and FIG. 3).

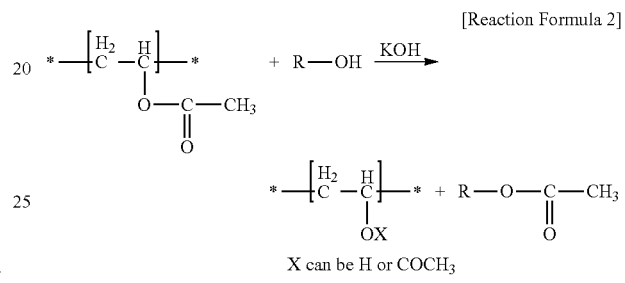

[Reaction Formula 2]

X can be H or $COCH_3$
* Partially-hydrolyzed PVA: Semi-crystalline
* Fully-hydrolyzed PVA: Highly crystalline For example, the poly(vinyl alcohol) may be Poval (Mowital) of Kuraray, Elvanol of DuPont, Selvol of Sekisui or others, but not be limited thereto.

In an embodiment of the present disclosure, the solvent of the poly(vinyl alcohol) may include a member selected from the group consisting of water, dimethyl sulfoxide (DMSO), ethanol, methanol, and combinations thereof, but not be limited thereto. The solvent may vary depending on grades and maximum solubility. A melting temperature ($T_m$) of the film, which has been made of the poly(vinyl alcohol) and completely dried, is about 220° C., and a glass transition

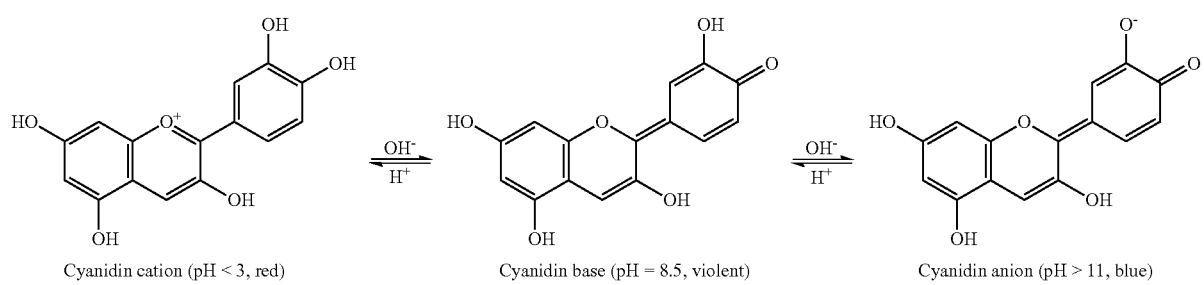

[Reaction Formula 1]

Cyanidin cation (pH < 3, red)　　Cyanidin base (pH = 8.5, violent)　　Cyanidin anion (pH > 11, blue)

temperature ($T_g$) thereof is about 85° C.; however, if water exists, the glass transition temperature ($T_g$) decreases to about 10° C. or less.

Figure 4:
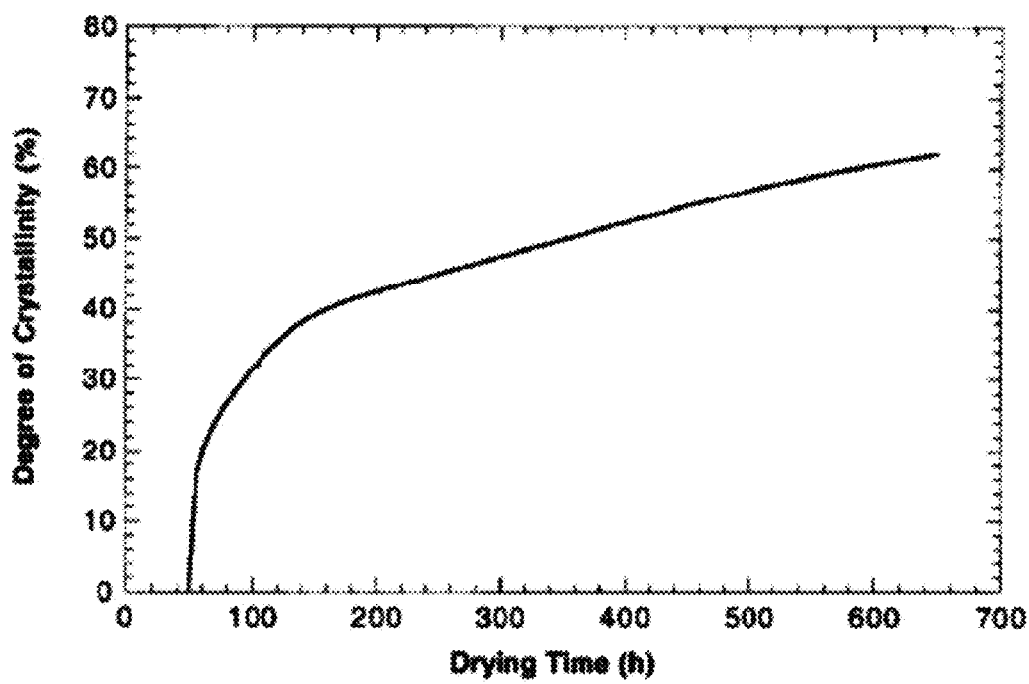
FIG. 4 shows change of crystallinity according to dry time, in an embodiment of the present disclosure.

In an embodiment of the present disclosure, upon the dry of the poly(vinyl alcohol), water exists due to the presence of the solvent, and as a result, chains easily move; and as the glass transition temperature also decreases, the chains more easily move even at the same temperature, and thus, the crystallization proceeds easily. FIG. 4 shows that the crystallinity also increases as the drying time increases. Even if drying a sample is carried out at an identical temperature, the crystallization may proceed much more as the drying rate is low. For example, when a sample having an about 10% water content is dried to have an about 0.1% water content, higher crystallinity can be achieved when the sample is dried for about 10 hours than that achieved when the sample is dried for about 1 hour. With respect to a method of adjusting the drying time, there may be a method of injecting a silica gel into a sample to adjust the drying time according to an injection amount or schedule of the silica gel, or a method of carrying out the drying while adjusting humidity within a humidity chamber.

In an embodiment of the present disclosure, the poly(vinyl alcohol) may be subject to annealing process after it is mixed with the dye so as to increase the crystallinity. In addition, the crystallinity of the film in accordance with an embodiment may significantly increase with increase of an annealing temperature and time.

In an embodiment of the present disclosure, through adjustment of the humidity upon the annealing process, sufficient crystallinity can be obtained even in case of low-temperature annealing. That is, if a certain amount or more of water exists upon the annealing, a sufficient annealing effect can be achieved even at a low temperature. For example, if water exists, the glass transition temperature of the poly(vinyl alcohol) decreases to a temperature around about 10° C. due to a plasticizing effect by the water. Accordingly, the movement of the chains becomes active even at a temperature far lower than the dry annealing temperature so that the crystallization can proceed. In case of the dry-annealing, the annealing should be carried out at about 80° C. or higher, which corresponds to the glass transition temperature of the dried poly(vinyl alcohol), resulting in the increase of the crystallinity. On the other hand, in case of the wet-annealing, since the increase of the crystallization can be induced even at a far lower temperature, the color change dye, which is sensitive to heat, can be used.

In an embodiment of the present disclosure, the poly(vinyl alcohol) is a highly unusual polymer in terms of its physical properties, and a polymer, which has stereoregularity and is atactic, may also proceed with the crystallization. That is, a poly(vinyl alcohol) film produced from water or water/a polar solvent has a partial crystalline structure as shown in FIG. 1, and thereby, forming a kind of a physical crosslinking point, and exhibits a similar behavior to that of a polymer crosslinked at a room temperature even without chemical crosslinkage.

In FIG. 1, the dots correspond to crystallized areas, non-crystallized areas exist based on the crystallized areas, and the parts that seem like pores in FIG. 1 can retain a sufficient amount of water.

In an embodiment of the present disclosure, as another example for the water-soluble polymer, the poly(vinyl butyral) is produced by converting poly(vinyl acetate) into poly(vinyl alcohol), and then, converting the poly(vinyl alcohol) once again, and may be substantially a terpolymer of vinyl alcohol, vinyl acetate, and vinyl butyral. While this material is not dissolved in water, it can be dissolved in a polar solvent according to a molecular weight and a conversion rate. When the material is produced to be a thoroughly dried film, the film has a water content of about 0.5% within about 24 hours, and since the film may contain more water depending on time and humidity, it may have a sufficient water content.

For example, as the poly(vinyl butyral), Mowital of Kuraray, Butvar of Eastamann or others may be used, but the poly(vinyl butyral) may not be limited thereto.

In an embodiment of the present disclosure, in case of the poly(vinyl butyral), a spin coating method may be used when the film is produced, but the present disclosure may not be limited thereto.

In an embodiment of the present disclosure, the solvent of the poly(vinyl butyral) may include toluene or alcohol, but not be limited thereto.

In an embodiment of the present disclosure, the water resistance of the poly(vinyl butyral) may be improved by coating the poly(vinyl butyral) on the film produced by using poly(vinyl alcohol), but the present disclosure may not be limited thereto.

Another aspect of the present disclosure provides a method for producing a composite for a harmful material-detecting sensor, which includes: adding a dye to a water-soluble polymer solution to obtain an aqueous solution of the water-soluble polymer and the dye; applying the aqueous solution of the water-soluble polymer and the dye onto a substrate to form a composite film; and annealing the composite film as a post-treatment.

In an embodiment of the present disclosure, the method may further include carrying out a dry-annealing or a wet-annealing process of the composite film, but may not be limited thereto.

In an embodiment of the present disclosure, the annealing may enhance a crystallinity of the composite film, but the present disclosure may not be limited thereto. In addition, the water resistance of the composite film may be improved with the improvement of the crystallinity, but the present disclosure may not be limited thereto.

All the descriptions of the composite for the harmful material-detecting sensor may be applied to the producing method in accordance with another aspect of the present disclosure.

Still another aspect of the present disclosure provides a harmful material-detecting sensor, which includes the above-described composite for the harmful material-detecting sensor in accordance with an aspect of the present disclosure.

In an embodiment of the present disclosure, in case of the harmful material-detecting sensor, the color of the dye changes by a reaction between the dye of the composite for the harmful material-detecting sensor and the harmful material, and the presence of the harmful material is identified from the change of the color of the dye, but may not be limited thereto.

All the descriptions regarding the composite for the harmful material-detecting sensor in accordance with an aspect of the present disclosure and the producing method in accordance with another aspect of the present disclosure as described above may be applied to the harmful material-detecting sensor in accordance with still another aspect of the present disclosure.

Hereinafter, the present disclosure is described more in detail with reference to Examples, but may not be limited to the Examples.

EXAMPLES

Example 1

1. Preparation of a PVA-Dye Aqueous Solution

For preparation of polyvinyl alcohol) (PVA), Mowiol 4-88 (a degree of hydrolysis is 85% to 89%, a molecular weight=31,000) powders (10 g) were slowly added to cold water (50 g) to avoid formation of lumps. Once the powders were fully dispersed in the water, the temperature of the water was increased to 50° C. while the dispersed solution was stirred. While maintaining the temperature, the stirring was continued for 2 hours so that a PVA solution was prepared. After the prepared PVA solution was cooled to a room temperature, a 0.5 wt % to 4 wt % color change dye (Bromophenol green) based on the PVA solid as added to the PVA solution so that a PVA-dye aqueous solution was prepared.

2. Production of a Film from the PVA-Dye Aqueous Solution

A solvent casting process was carried out by adding 5 g of the aqueous solution prepared as described above to a mold, which was made by attaching a polyimide tape onto an edge of a square (10 cm×10 cm) PMMA sheet(thickness 0.5 T, casting test Printec co.). After the material that had been subject to the above-described process was dried at a room temperature for 30 minutes, it was dried in a 90° C. oven for 1 hour so that a PVA-dye film was produced.

Example 2

1. Dry-Annealing for the PVA-Dye Film

The PVA-dye films dried in the oven as described above were subject to follow-up processing through annealing at different temperatures for different time periods, and Table 1 below shows crystallinity according to the annealing temperatures and time periods. The crystallinity of the film produced by the method of Example 2 also significantly increased with the increase of the annealing temperature and time.

TABLE 1

| Annealing Temperature (° C.) | Time (minutes) | Crystallinity (by DSC) |
| --- | --- | --- |
| 90 | 30 | 35% |
| 100 | 60 | 47% |
| 120 | 30 | 50% |
| 120 | 90 | 71% |

2. Wet-Annealing for the PVA-Dye Film

Sufficient crystallinity could be achieved even at low-temperature annealing through adjustment of humidity upon the annealing process. Table 1 above shows results of dry-annealing that was carried out in a convection oven, in which humidity was not controlled, and Table 2 below shows results of wet-annealing that was carried out in a humidity chamber under adjusted humidity, which means that when a certain amount or more of water exists, a sufficient annealing effect can be achieved even at a low temperature. That is, when water exists, the glass transition temperature of PVA is decreased to a temperature around about 10° C. as a result of a plasticizing effect by the water. Accordingly, the movement of the chains becomes active even at a far lower temperature than the dry-annealing temperature so that the crystallization proceeds. While the dry-annealing could result in the increase of the crystallinity when it was carried out at about 80° C. or more, which corresponds to the glass transition temperature of the dry PVA, the wet-annealing could induce the increase of the crystallinity even at a far low temperature, so that the color change dye, which is sensitive to heat, could also be used.

TABLE 2

| Annealing Temperature (° C.) | Humidity (%, relative) | Time (minute) | Crystallinity (by DSC*) |
| --- | --- | --- | --- |
| 40 | 80 | 60 | 53% |
| 50 | 90 | 60 | 65% |

In Table 2 above, the crystallinity was measured after the sample, for which the wet-annealing was finished, was dried in vacuum at a room temperature.

Example 3

Production of a PVA-Dye-Containing Double Layered Film

In order to form a protecting film on the PVA-dye film produced in Example 1 above, 2 g Selvol E325 (Kuraray, a degree of hydrolysis=98%) was added to 50 g water so that an aqueous solution was prepared by the same method as used in Example 1. 5 g of the aqueous solution prepared as described above was administered onto the film produced in Example 1, and the film was dried at a room temperature for 30 minutes, and thereafter, further dried in a 120° C. oven for 90 minutes so that a double layered film was produced.

Example 4

Production of a PVB-Dye-Containing Film 1 g PVB (Mowital B30HH, Kuraray) was added to 10 ml ethanol, to which 0.1 M NaOH was added, and stirred at a room temperature to be dissolved therein. A 4 wt % color change dye based on the PVB solid was added to the obtained ethanol solution. For spin-coating of the mixture solution, the solution was coated on a corona-treated PET film as a substrate at 1,500 rpm for 8 seconds, and dried at a room temperature so that the film was obtained.

Poly(vinylbutyral) is produced by converting poly(vinyl acetate) into poly(vinyl alcohol), and then, converting the poly(vinyl alcohol) once again, and may be substantially a terpolymer of vinyl alcohol, vinyl acetate, and vinyl butyral. While the poly(vinyl butyral) is not dissolved in water, it can be dissolved in a polar solvent according to a molecular weight and a conversion rate; when the poly(vinyl butyral) is produced to be a thoroughly dried film, the film has a water content of about 0.5% within about 24 hours; and since the film may contain more water depending on time and humidity, it may have a sufficient water content (Table 3). For the poly(vinyl butyral), in addition to Mowital of Kuraray, Butvar of Eastaman or others may be used, and Table 3 below shows physical properties of the Butvar products of Eastaman as examples for the poly(vinyl butyral).

TABLE 3

|  | B-72 | N-74 | B-76 | B-29 | B-90 | B-90 |
| --- | --- | --- | --- | --- | --- | --- |
| Molecular weight | 170-250 | 120-150 | 90-120 | 50-80 | 70-100 | 40-70 |

TABLE 3-continued

| | B-72 | N-74 | B-76 | B-29 | B-90 | B-90 |
|---|---|---|---|---|---|---|
| (weight average × 1,000) | | | | | | |
| Hydroxyl group content (%) | 17.5-20.0 | 17.5-20 | 11.5-13.5 | 11.0-13.5 | 18.5-20.5 | 18-20 |
| Acetate content (%) | 0-2.5 | 0-2.5 | 0-2.5 | 0-2.5 | 0-2.5 | 0-2.5 |
| Butyral content (%) | 80 | 80 | 88 | 88 | 80 | 80 |
| Water absorption (24 hours, %) | 0.5 | 0.5 | 0.3 | 0.3 | 0.5 | 0.5 |
| Glass transition temperature (° C.) | 72-78 | 72-78 | 62-72 | 62-72 | 72-78 | 72-78 |
| Heat deflection temperature (° C.) | 56-60 | 56-60 | 50-54 | 50-54 | 52-56 | 45-55 |

EXPERIMENTAL EXAMPLES

Experimental Example 1

Harmful Material-Detecting Test for the PVA-Dye-Containing Double Layered Film

Figure 5:
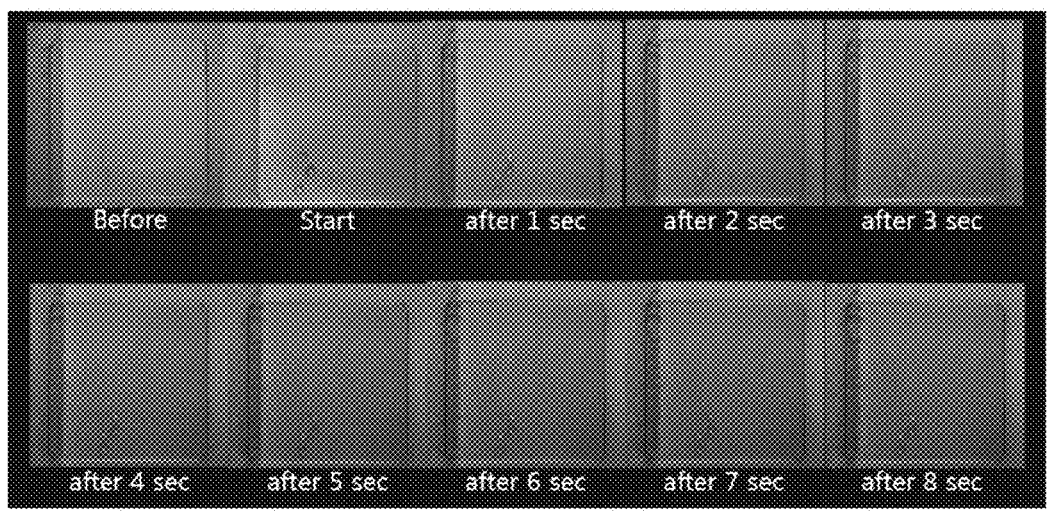
FIG. 5 shows color change of a film produced in an Example according to time after the film is exposed to ammonia vapor, in an embodiment of the present disclosure.

After the film produced in Example 3 above was exposed to ammonia vapor, color change of the film was observed according to time. FIG. 5 shows results of the color change. The film produced in Example 3 above exhibited a reaction that can be observed by eyes within 4 seconds after the exposure.

Experimental Example 2

Harmful Material-Detecting Test of the PVB-Dye-Containing Film

FIG. 6B shows standard color change of the color change dye used in Example 4. FIG. 7 shows color change when the film produced in Example 4 above was exposed to an acid or base.

Experimental Example 3

Influence on the Water Resistance Depending on Annealing

In order to determine how the crystallinity increased by the annealing affects the water resistance, three (3) samples were prepared as set forth below, and after the samples were immersed in water for 1 minute at the same time, they were taken out of the water to be observed by eyes. To facilitate the eye observation, bromophenol blue was use as a dye, and a 4 wt % dye based on the solid was added to each of the samples. After all the three samples were dried by using the PVA-dye aqueous solution produced by the method of Example 1 at a room temperature for 30 minutes, the follow-up processing method below was applied to the samples (FIG. 8):

Sample 1: Dried at a room temperature for 5 hours, and then, dried in a vacuum oven at a room temperature for 12 hours;

Sample 2: Dried in a 90° C. convention oven for 60 minutes, and then, dried in a vacuum oven at a room temperature for 12 hours; and Sample 3: Dried in a 90° C. convection oven for 60 minutes, and then, subject to dry-annealing at 120° C. for 60 minutes, and dried in a vacuum oven at a room temperature for 12 hours.

FIG. 8 shows results of eye observation of the samples. It was identified that Sample 3, which is expected to achieve the highest crystallinity, was damaged little, whereas the films of Samples 1 and 2, which achieved relatively low crystallinity, were partially dissolved in water.

Experimental Example 4

Figure 9:
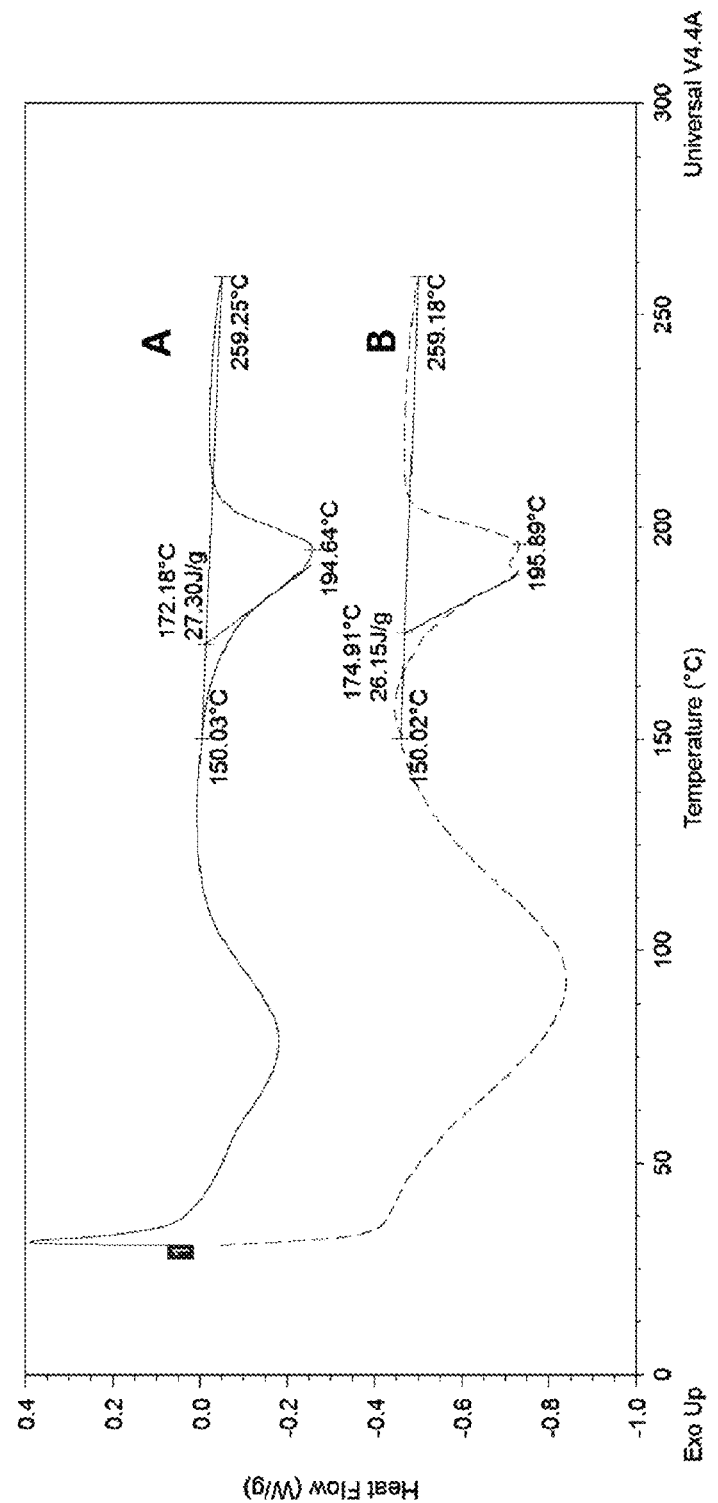
FIG. 9 is a graph showing change of crystallinity according to a condition for annealing a film, in an Example of the present disclosure.

Influence on the Crystallinity Depending on a Humidity Condition Upon the Annealing In order to determine change of the crystallinity depending on the humidity condition upon the annealing, FIG. 9 shows thermal analysis (DSC) data obtained by preparing two (2) samples as described below and comparing them with each other. After the two samples were dried by using the PVA-dye aqueous solution prepared by the method of Example 1 at a room temperature for 30 minutes, the follow-up processing method below was applied thereto (FIG. 9):

Sample A (Dry-annealing): Dried in a 90° C. convection oven for 60 minutes, and then, subject to dry-annealing at 120° C. for 60 minutes, and dried in a vacuum oven at a room temperature for 12 hours; and Sample B (Wet-annealing): Dried in a 90° C. convection oven for 60 minutes, and then, subject to wet-annealing in a humidity chamber, in which the humidity was adjusted to 90% relative humidity, at 50° C. for 60 minutes, and dried in a vacuum oven at a room temperature for 12 hours.

FIG. 9 shows that the crystallinity upon the dry-annealing at 120° C. and the crystallinity upon the wet-annealing at 50° C. were similar to each other.

Experimental Example 5

Change of the Crystallinity According to the Dry-Annealing

Each of the PVA-dye films, which were produced by drying the PVA-dye aqueous solution prepared by the method of Example 1 at a room temperature for 12 hours, and then, drying the same in a 60° C. convection oven for 24 hours, was subject to dry-annealing under the following conditions (FIG. 10):

Sample A: Subject to dry-annealing process in a 140° C. convection oven for 30 minutes;

Sample B: Subject to dry-annealing process in a 140° C. convection oven for 1 hour; and Sample C: Subject to dry-annealing process in a 140° C. convection oven for 3 hours.

Figure 10:
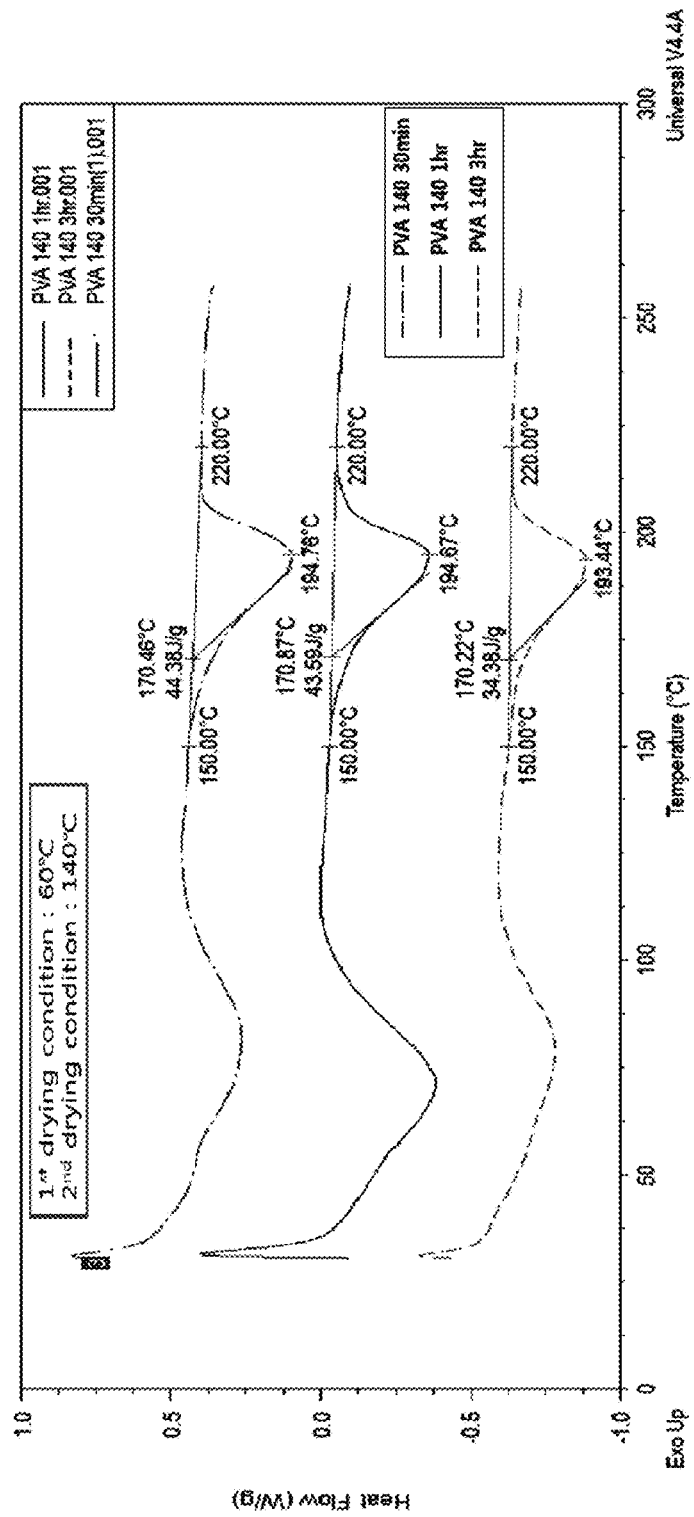
FIG. 10 is a differential scanning calorimetry (DSC) thermal analysis graph showing crystallinity of a PVA-dye film according to dry-annealing process, in an Example of the present disclosure.

FIG. 10 is a differential scanning calorimetry (DSC) thermal analysis graph showing the crystallinity of the PVA-dye film in accordance with Experimental Example 5.

Experimental Example 6

Change of the Crystallinity According to the Wet-Annealing

Each of the PVA-dye films, which were produced by drying the PVA-dye aqueous solution prepared by the method of Example 1 at a room temperature for 12 hours, and then, drying the same in a 60° C. convection oven for 24 hours, was subject to wet-annealing under the following conditions (FIG. 11):

Sample A: Subject to wet-annealing process in a humidity chamber, in which the humidity was adjusted to 80% relative humidity, at 140° C. for 30 minutes;

Sample B: Subject to wet-annealing process in a humidity chamber, in which the humidity was adjusted to 80% relative humidity, at 140° C. for 1 hour; and Sample C: Subject to wet-annealing process in a humidity chamber, in which the humidity was adjusted to 80% relative humidity, at 140° C. for 3 hours.

Figure 11:
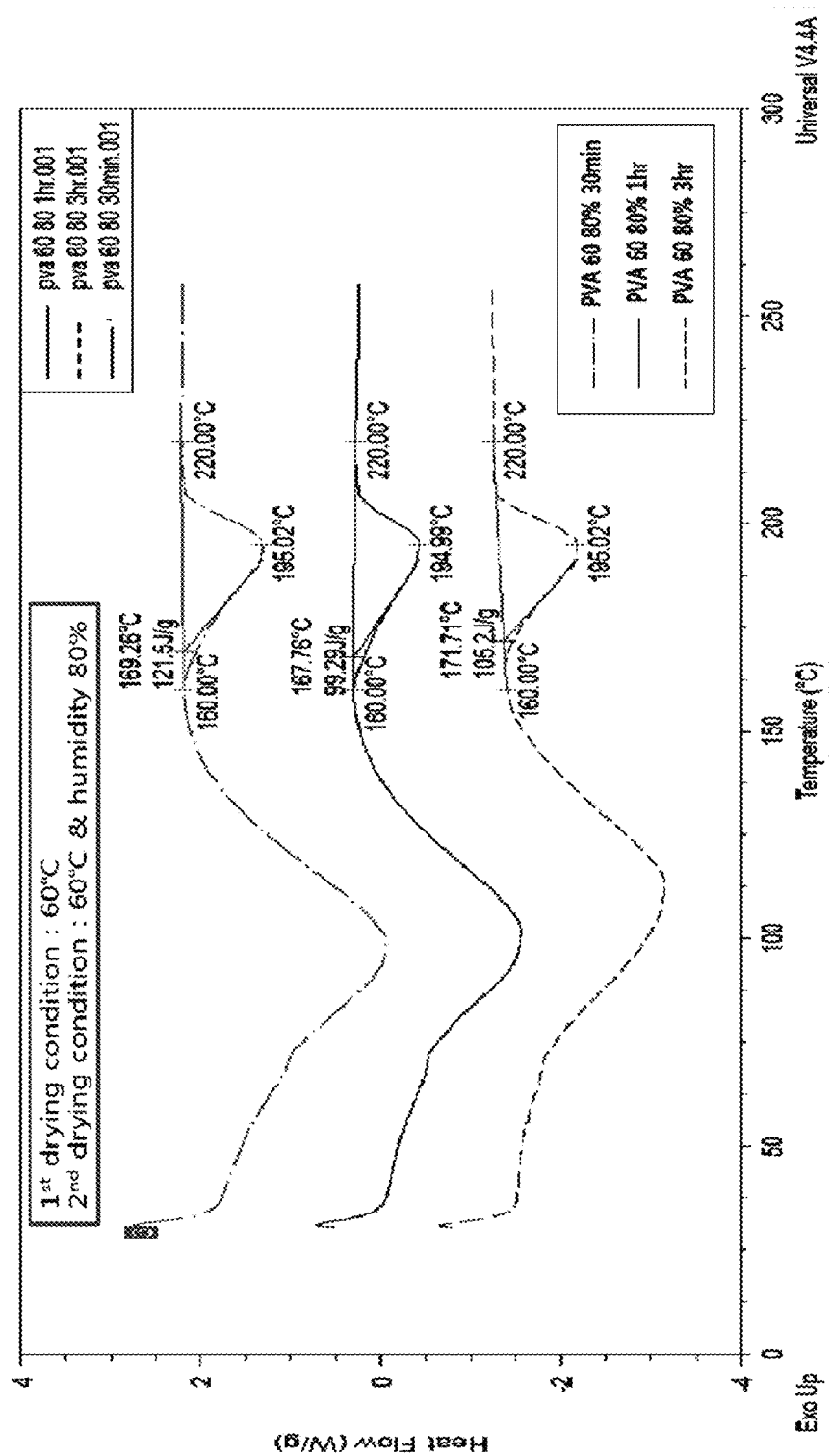
FIG. 11 is a DSC thermal analysis graph showing crystallinity of a PVA-dye film according to wet-annealing process, in an Example of the present disclosure.

FIG. 11 is a DSC thermal analysis graph showing the crystallinity of the PVA-dye film in accordance with Experimental Example 6. It was identified that compared to the dry-annealing in Experimental Example 5, the crystallinity of the film, which was subject to the wet-annealing at the same annealing temperature according to Experimental Example 6, was improved about 2 or 3 times.

Experimental Example 7

Influence 2 on the Crystallization According to the Humidity Condition Upon the Annealing Each of the PVA-dye films, which were produced by drying the PVA-dye aqueous solution prepared by the method of Example 1 at a room temperature for 12 hours, and then, drying the same in a 60° C. convection oven for 24 hours, was subject to annealing for 1 hour under the following conditions:

Sample A: Subject to dry-annealing process in a 140° C. convection oven;

Sample B: Subject to wet-annealing process in a humidity chamber, in which the humidity was adjusted to 80% relative humidity, at 80° C.; and Sample C: Subject to wet-annealing process in a humidity chamber, in which the humidity was adjusted to 80% relative humidity, at 60° C.

Figure 12:
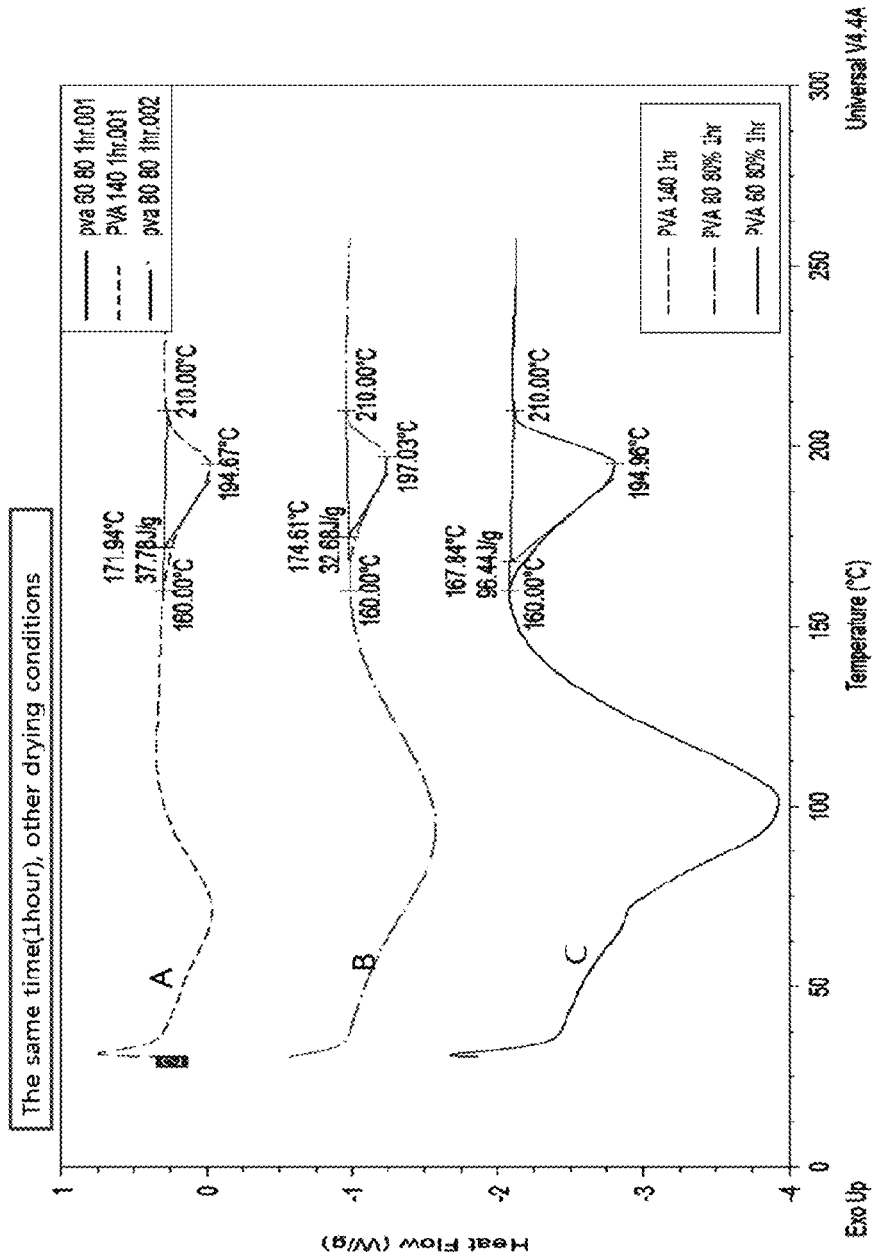
FIG. 12 is a DSC thermal analysis graph for comparison of crystallinity of PVA-dye films, which have been subject to annealing process under different annealing conditions, in an Example of the present disclosure.

FIG. 12 is a DSC thermal analysis graph obtained by comparing the crystallinity of the PVA-dye films, which were subject to the annealing process under the different annealing conditions according to Experimental Example 7, and shows that the crystallinity is improved as the annealing temperature upon the wet-annealing is low.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

We claim:

1. A composite film for a harmful material-detecting sensor, comprising:
   a polymer matrix comprising a dye dispersed in a water-soluble polymer,
   wherein the polymer matrix is permeable to the harmful material, and
   wherein the polymer matrix is configured to be resistant to dissolution in water by a wet-annealing process, which thereby induces an increase in a crystallinity of the film.

2. The composite film of claim 1, wherein the water-soluble polymer includes poly(vinylalcohol) or poly(vinylbutyral).

3. The composite film of claim 1, wherein the dye reacts with the harmful material to exhibit its color change.

4. The composite film of claim 3, wherein the harmful material includes a member selected from the group consisting of ammonia ($NH_3$), hydrochloric acid (HCl), hydrofluoric acid (HF), formaldehyde (HCHO), chlorine ($Cl_2$), hydrogen sulfide, dimethyl amine, diethyl amine, triethyl amine, methyl amine, sulfur dioxide, nitric acid, and combinations thereof.

5. The composite film of claim 1, wherein the film is crystallized.

6. The composite film claim 1, wherein the film includes a single film layer or multiple film layers.

7. A method for producing a composite for a harmful material-detecting sensor, comprising:
   adding a dye to a water-soluble polymer solution to obtain an aqueous solution of the water-soluble polymer and the dye;
   applying the aqueous solution of the water-soluble polymer and the dye onto a substrate to form a composite film; and
   annealing the composite film as a post-treatment in order to enhance a crystallinity of the film and render the film resistant to dissolution in water.

8. The method of claim 7, further comprising carrying out a dry-annealing or a wet-annealing process of the composite film.

9. A harmful material-detecting sensor, comprising the composite film for the harmful material-detecting sensor according to claim 1.

10. The harmful material-detecting sensor of claim 9, wherein, upon reaction with the harmful material a color of the dye changes, and
   wherein a presence of the harmful material is detected based on the color change of the dye.

11. The composite film of claim 1, wherein the polymer matrix is resistant to dissolution in water for at least 1 minute.

* * * * *